United States Patent [19]

Dinzburg et al.

[11] Patent Number: 5,495,772
[45] Date of Patent: Mar. 5, 1996

[54] APPARATUS AND METHOD FOR MEASURING THE CURE STATE FOR ELASTOMERIC ARTICLES

[75] Inventors: Boris Dinzburg, Niles; Jone Deng, Hoffman Estates, both of Ill.

[73] Assignee: SKF USA Inc., Elgin, Ill.

[21] Appl. No.: 328,466

[22] Filed: Oct. 25, 1994

[51] Int. Cl.⁶ ............................................ G01N 3/32
[52] U.S. Cl. .......................... 73/832; 73/826; 73/865.8
[58] Field of Search ................. 73/865.9, 86, 766, 73/781, 785, 788, 817, 822, 865.8, 866, 87, 796, 805, 826, 832, 833, 835, 814, 847

[56] References Cited

U.S. PATENT DOCUMENTS

| | | | |
|---|---|---|---|
| 922,524 | 5/1909 | Schopper | 73/832 |
| 2,506,048 | 5/1950 | Van Den Akker . | |
| 2,677,187 | 5/1954 | Buist et al. | 73/832 |
| 3,423,997 | 1/1969 | Mauer | 73/826 |
| 3,693,424 | 9/1972 | Wagle | 73/832 |
| 3,933,032 | 1/1976 | Tschoegl | 73/774 |
| 3,969,930 | 7/1976 | Prevorsek et al. | 73/826 |
| 4,030,348 | 6/1977 | Fletcher et al. | 73/826 |
| 4,059,983 | 11/1977 | Fritzsche | 73/815 |
| 4,122,705 | 10/1978 | Rober | 73/832 |
| 4,546,438 | 10/1985 | Prewitt et al. | 73/815 |
| 4,730,498 | 3/1988 | Blanch . | |
| 5,178,017 | 1/1993 | Dinzburg . | |
| 5,351,553 | 10/1994 | Lepie et al. | 73/826 |

Primary Examiner—Richard Chilcot
Assistant Examiner—George M. Dombroske
Attorney, Agent, or Firm—James T. FitzGibbon

[57] ABSTRACT

A method and apparatus for rapidly determining the cure state of an annular rubber or elastomeric article is provided. The article is placed so that an inner hole portion fits over separable parts of a test fixture, and tension is induced in a stepwise manner by moving the separable parts apart in discrete incremental steps. The tension is allowed to relax between the steps. By generating a force/deflection curve in this way, the user may optimize the cure state of the tested articles by controlling the cure time and temperature of a manufacturing process in response to the measured data.

10 Claims, 3 Drawing Sheets

LOW FORCE DECAY

FIG. 7

HIGHER FORCE DECAY

APPARATUS AND METHOD FOR MEASURING THE CURE STATE FOR ELASTOMERIC ARTICLES

The present invention relates generally to test methods and apparatus, and more particularly, to an analyzer and method for rapid, non-destructive determination of the "state of cure" of finish molded rubber articles, particularly those of annular configuration such as seals, O-rings, gaskets and the like.

According to the invention, a finish molded rubber article, or more commonly, the molded rubber component of a composite, insert-molded article, can be tested immediately after manufacture to determine its state of cure, i.e., the degree to which the elastomer is cross-linked. This information can then be used, at the extremes, to accept or reject finished articles, but more commonly, to control quality by making whatever adjustment to processing apparatus and methods appear necessary to attain and/or maintain a desired degree of cross-linking in the final product.

In other words, the manufacturing apparatus and method can be "fine-tuned" by increasing or decreasing the process temperature or the molding time, or both, if, when and to the extent needed to continue the production of high quality articles. Thus, if the completed product appears slightly under-cured, i.e., at the lower end of a preferred range of cure states, subsequently made articles can be more fully cured by increasing their residence time in the mold, increasing the mold temperature, or both.

Likewise, if over-cured products are being products, the articles in process can be subjected to a shorter duration molding cycle, a lower temperature, or both. In this way, the products can be kept within acceptable limits by fine adjustments to the curing process so that a trend toward an under- or over-cured product does not continue until unacceptable products are being made.

In general, the first step in the method of the invention is to determine a desirable state of cure which the product should have. This can initially be done by destructive tests or other methods which are not suitable for use in controlling quality during production. After the desired state of cure has been determined, this state can be expressed in terms of a degree of cross-linking. Then, according to the method of the invention, articles are subjected to a rapid and easily performed test to determine the degree to which they correspond to the behavior of an ideally cured product.

Basically, the method of the invention involves taking a series of force/deflection measurements on the cured article and connecting certain points to determine the slope of a force/deflection curve. This slope is then compared with the slope of a force/deflection curve for an article which has been tested by other methods and found to be ideal. The exact values or slopes of the force/deflection curves, of course, vary considerably among different products, because of variations in the materials being used, and the size and cross-section of the product. Thus, certain rubber materials are more stiff than others. Using the same method, a small diameter seal with a thick cross-section will be much stiffer than will a large diameter seal with a thin cross-section. However, the absolute slope of the force/deflection curve for articles of the same size, shape and material which have the same cross-link density will be the same.

In the preferred form, the force/deflection curve is prepared by taking plural readings on an annular specimen using a split shaft and a load cell. The specimen is preferably placed in a heated chamber, allowed to reach temperature equilibrium, deflected a predetermined amount and allowed to relax for a brief time before a force reading is taken. The process is repeated such that there are successive movements of the split shaft with equal relaxation times being allowed-between measurements.

Each measurement of the stress is taken after equal periods of relaxation time. The graph thus prepared will may yield a comparatively straight line having a given slope (y/x). The slope of this line is entered as a datum on a reference chart wherein various articles are compared with the different degrees to which the elastomer in the product is cross-linked, measured by a standard research method.

By way of background, the properties of a rubber composition generally depend upon the degree to which the rubber is cross-linked. The reaction by which a rubber composition is cured involves a change of the material from a plastic state into that of an elastomer. Elastomers of this kind are thermoset materials wherein various long polymer chains are cross-linked to one another to form a three-dimensional molecular network.

The extent to which cross-linking takes place depends on several factors, including the nature of the formulation and the cure conditions. The nature of the formulation determines the maximum potential for cross-linking. The optimal cure time almost never results in the maximum possible degree of cure, only a desirable degree of cure. Products having less than the optimum amount of cross-linking are under-cured and tend to retain at least some characteristics of a plastic, whereas products that are over-cured may tend to become unduly hard or brittle.

Given a particular set of process conditions, i.e., cure time and temperature, a desired cure state can usually be achieved, other things being equal. However, generally speaking, if the curing temperature is too low, or the curing period is too short, an under-cured condition will result, whereas excess curing time or unduly high temperatures may create an over-cured condition.

While the ideal degree of cure may be different for rubbers based on different polymers, and may be different, even where the same or similar polymers are used to make different products, there is almost always an optimal degree of cure for a particular product made from a particular material.

During manufacture, it would be very advantageous if process conditions could be continually monitored and changed so as to produce only products that were cured to an ideal state or to an exactly desired degree. However, there are many variables at work in rubber processing, and attempts to achieve ideal cure state by manipulating the conditions without continually sampling the product have not always been successful.

It is believed that any approach based on the concept of attempting to reproduce certain ideal conditions exactly will simply not operate successfully in mass production as a practical matter. Consequently, it is accepted that the actual cure state of a given finished article taken from a batch of articles being produced under certain conditions must be determined in order to determine, on an instantaneous basis, whether the article is ideally cured, under-cured or over-cured. Thus, given an ideal state of cure for any one product, random samples can be taken from the output of a production line and tested to determine whether cure conditions should be altered and, if so, whether the condition should be changed to increase or decrease the cure state.

Unfortunately, this theory has not usually been able to be carried into practice. Determining the exact cure state of finished articles has been not only a somewhat problematical procedure, but more importantly, it has required destructive testing. Equally important, the time required for the test—sometime typically about a week—completely eliminates the use of such procedure as a control in a production process. Quite clearly, instantaneous or ongoing monitoring and correction of production conditions, ideally carried out every few minutes, cannot be practical if it takes a week to determine that such conditions should be changed. If this were the case, by the time the need for a change were detected, tens of thousands of less than satisfactory articles might have been produced.

Referring in particular to a prior art method of measuring cure state, a method known as the Flory-Rehner method has been utilized. This method requires immersing a cured rubber product in solvent and determining over time the extent to which it swells the equilibrium. While the Flory-Rehner method is considered relatively reliable and accurate, its destructive nature and excessive time delay rule it out for practical use as a control in a production process.

Another known method is observing the change in the modulus of rubber. This method is also destructive, and also cannot be applied to small articles such as seals or the like. The specimens tested by this method are of a particular size and shape not resembling the shape of seals, O-rings, and like articles.

Referring now to other aspects of rubber curing, because the cure process involves heat transfer from surfaces of the mold to the product, the surface-to-volume ratio of the article is important. Accordingly, where the actual articles to be tested do not resemble a test specimen in size or shape, and wherein the molds used to make the test specimen and the article differ greatly in various respects, a method depending on congruent specimen shapes is simply not useful. Methods involving change of hardness have been proposed and are useful from a theoretical standpoint, but such methods are destructive and are usually not sufficiently sensitive to be of value. In many tests using these methods, the variation in data creates a spread that is too wide to be useful.

Ideally, if a desired degree of cross-linking could be established for a given product, and a proper test were able to be performed in minutes that would accurately reflect such a degree of cross-linking, then highly advantageous manufacturing techniques could be adopted. Knowledge of the optimal cure state and a non-destructive method of testing for correspondence to such cure state would enable meaningful tests to be made on products just removed from a production line. Ideally, within a few minutes of removing articles, testing would be completed and process conditions could then be adjusted if necessary before the conditions varied to the extent that unsatisfactory articles were being produced.

An industry in which the cure state of rubber articles is an important consideration is the oil seal industry. This industry is one which has pioneered the practical application of a number of synthetic elastomers, some of which are considered either quite exotic, and other of which are formulated for meeting the needs of highly specialized applications. Because the need to seal fluids such as oil, grease, water, and other materials is an exceptionally important requirement in many industrial mechanisms, including automotive and aircraft engines, hydraulic systems, and the like, a great deal of effort has gone into providing seals for such mechanisms. In many cases, a seal that is comparatively inexpensive is called upon to prevent leakage, which, if permitted to occur, would damage a mechanism having a value many hundreds or thousands of times that of the value of the seal.

Satisfying the need to seal fluids for applications such as these has often required the use of novel elastomers. Inasmuch as many oil and grease seals are comparatively small in size, the seal industry is one wherein elastomers which would be too expensive for other applications can be cost-justified. In other words, even if an elastomer costs from ten or twenty, up to a hundred dollars or more per pound, its use may be justified by the urgency of the particular seal application; this is especially true because many seals are so small that they require only a small fraction of an ounce of such elastomer.

However, even where comparatively expensive elastomers are used, because of their chemical nature, great care must be taken in their manufacture. Synthetic elastomers, as used in most sealing applications, contain a variety of fillers of various kinds, including those intended to provide extra strength, lubricity, abrasion-resistance or the like. In addition, the elastomer formulation contains not only one or more base polymers, but also whatever combination of cross-linking agents is necessary to achieve cure. Still further, most elastomers include various other additives, such as accelerators, anti-oxidants or anti-ozonants, mold release agents, and processing aids for improving the rheological properties of the elastomer formulation during molding. These can cause the finished, cured product to have properties quite different from those that the pure elastomer itself would be expected to have.

By way of further background, during manufacture of a typical oil seal, a casing or like rigid member is positioned relative to a mold such that a small portion of the casing extends into the molding cavity. Two or more movable mold parts are closed over opposed faces of the casing flange so as to form a barrier against escape ("flash") of curable fluent elastomer and the molding cavity is filled with elastomer and permitted to cure for a period of perhaps one to four minutes. In some cases, a "post cure" or oven baking process follows the initial curing. Molding temperatures vary considerably, but many synthetic elastomers are cured at temperatures of 275°–350° more or less. The curing process involves complex chemical kinetics and is dependent upon both time and temperature.

For various reasons, which include the fact that most rubbers are thermal insulators, and the fact that the shapes of the mold affect the manner in which heat is transferred to the polymers during the exothermic curing reaction, it is difficult to establish ideal molding conditions on theoretical basis. Hence, many aspects of a mold design, including its surface-to-interior volume ratio, the size and shape of the sprue areas through which the elastomer will be transferred into the cavity and the cure time and temperature are arrived at through experience and more or less educated "guess work".

When a finished seal is applied to a particular installation, it is subject to conditions of sometimes extreme temperature as well as exposure to various chemical reagents. If the elastomeric seal body is cured excessively or insufficiently, the elastomer will not perform properly and the seal will fail in use. In some cases, the seal may actually undergo a post-curing reaction after installation, causing it to become embrittled and hence it will seal unsatisfactorily. In this connection, it will be realized in that in spite of having fillers and other additions to its formulation, a satisfactory rubber for a seal application must always maintain its elastomeric characteristic. This is because it must follow shaft irregularities, both static and dynamic, and in some cases, deflect under the load of hydraulic and/or gravitational and inertial forces.

The seal functions by the application of a radial compressive load, but as the shaft moves relative to the bore throughout a range of dynamic conditions, the seal must follow such movements or leakage will occur. Hence, it is of paramount importance that the flexibility of the seal should lie substantially within a desired range at the highest and lowest temperatures reasonably expected to be encountered, and that it should continue to possess this elasticity over a period of many years.

Inasmuch as the cure state usually determines whether an elastomer will change its characteristics after being placed in the application, accurately determining the cure state after manufacture is of paramount importance. In the prior art, curing conditions have generally established by arriving at time/temperature parameters, making seals according to such parameters and periodically destructively testing the products or observing their performance in use.

However, this process has been less than completely satisfactory inasmuch as a great deal of time might elapse between production of the product and discovery that the product was under-cured or over-cured. This in turn resulted because there was no satisfactory, non-destructive method of testing products immediately after product.

Accordingly, it would be considered very beneficial by the seal industry if a non-destructive, quick, post-manufacturing test method could be used to insure that the products as manufactured did in fact possess the cure states desired rather than merely being able to ensure that process conditions believed to be appropriate had been followed. It would be further beneficial to the industry to develop a simple method which, by reason of its speed and accuracy potential, could be used as an adjunct to manufacture. By this is meant that, as the products were being manufactured, if a trend towards under- or over-cured were detected while the manufactured products were still within a satisfactory range, the trend could be reversed and, in effect, the quality control parameters of time and temperature to achieve satisfactory curing could be applied during the manufacturing process.

Inasmuch as the prior art has not provided a satisfactory method and apparatus for reliably testing the cure state of molded articles in a non-destructive manner, it is an object of the present invention to provide such a method of non-destructive cure state analysis.

Another object of the invention to provide an apparatus which will permit such testing to be achieved.

A further object of the invention is to provide a method of testing the state of cure of finished elastomeric articles having an annular configuration and possessing a variety of cross-sectional shapes.

A still further object of the invention is to provide a method of cure state testing which includes the steps of determining the slope of a force/deflection curve of sample elastomers, which method includes making observations or readings on a finished-molded article in a non-destructive way.

Another object of the invention is to provide a method wherein the force/deflection properties of a given elastomer are tested under conditions of elevated temperature, permitting systematic elimination of improper or misleading readings attributable to chemical and mechanical reactions between the molecular structure of the elastomer and its interaction with fillers or other elements in the finished product.

Yet another object of the invention is to provide an apparatus which includes an oven or like means for creating an elevated temperature zone, a test fixture disposed within the zone and characterized by an expansible split shaft for receiving the molded article, and remote means for separating the shaft halves or segments apart by a known increment, and a load cell to permit measurement of the initial and subsequent force levels generated by the specimen in reaction to the imposed deflection.

A still further object of the invention is to provide an apparatus which includes a split shaft for receiving thereover a specimen product such as a ring or seal, remote means such as a micrometer screw for urging the halves of the shaft to a spaced apart position so as to deflect the body of the test subjects and means disposed between the micrometer and the movable portion of the shaft so that the distorting force is applied through a load cell capable of indicating the forces required to be applied and/or maintained to achieve a given degree of deflection.

Another object of the invention is to provide a non-destructive analytical test method which involves comparing the slopes of various force/deflection curves of known samples to those of articles then being produced to determine the state of cure of the articles being produced by a simplified empirical comparison.

A still further object of the invention is to provide a method of improving the quality of production of molded rubber articles, which method includes the steps of periodically sampling and non-destructively testing molded articles to determine their cure state and thereafter adjusting process conditions to achieve a more or less highly cured condition of the product, without being required to stop production or decrease production speed while such analyses and corrections are being conducted.

The foregoing and other objects and advantages of the invention are achieved in practice by providing an apparatus which includes an oven or like means for establishing a temperature control zone, with such apparatus having a fixture therein which includes a split shaft and means for moving the split shaft parts away from each other to a predetermined degree and measuring the residual force remaining after relaxation so that data regarding physical properties can be determined, tabulated, and compared to a standard. The invention also achieves its objects and advantages by providing a method wherein a force/deflection curve is derived from several readings taken at an elevated temperature and the value of the slope of the resulting line curve is compared to a standard or predetermined slope to determine a relative state of cure.

The manner in which the foregoing and other objects and advantages of the invention are achieved in practice will become more clearly apparent when reference is made to the following detailed description of the preferred embodiments of the invention set forth by way of example and shown in the accompanying drawings, wherein like reference numbers indicate corresponding parts throughout.

DESCRIPTION OF THE PREFERRED EMBODIMENTS OF THE INVENTION

While the method of the invention may be performed using different forms of apparatus, a description will be given of one form of apparatus wherein fluid retention seals such as oil and grease seals are the articles to be tested, the relatively movable element is one half of a shaft split into two halves along a plane lying parallel to its longitudinal axis and wherein incremental movement of the shaft is accomplished by manipulating a micrometer screw mechanism extending through the sidewall of the controlled temperature apparatus.

Figure 1:
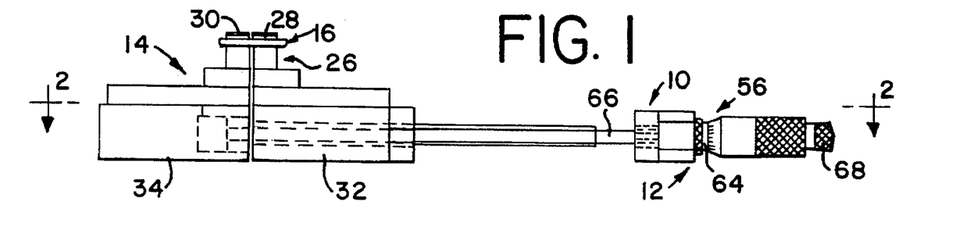
FIG. 1 is a top plan view of the test apparatus made according to the invention, and shown outside the climate control apparatus.
Figure 2:
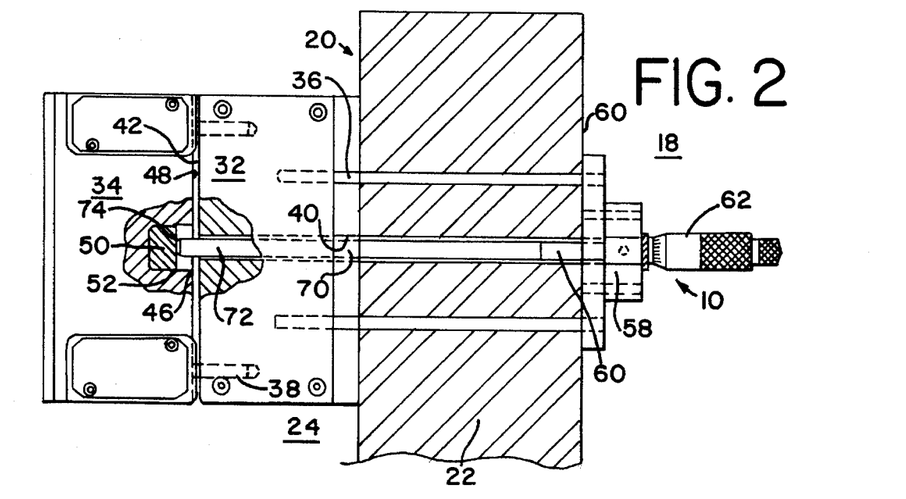
FIG. 2 is a front elevational view of the apparatus of FIG. 1, showing the apparatus relative to the oven and showing certain portions broken away for clarity.

Referring now to the drawings in greater detail, FIGS. 1 and 2 show portions of a test apparatus generally designated 10 and shown to include a control portion generally designated 12, a specimen holder portion generally designated 14 and adapted to receive a specimen 16 to be tested. According to the invention, it is preferred to position the control portion 12 in an area 18 outside an oven generally designated 20 and shown to include an insulated sidewall 22 and an oven interior 24 where a temperature may be carefully controlled.

An important aspect of the invention is that a test shaft generally designated 26 forms a part of the specimen holder 14 with the test shaft 26 being split so as to form inner and outer shaft halves 28, 30 respectively positioned by inner and outer carriers 32, 34. The fixed or inner carrier 32 is secured as by fasteners 36 to the oven wall 22. The fixed or inner carrier 32 preferably also includes at least two guide bores 38 and a central, rod-receiving opening 40. The inner carrier 32 terminates in a vertically extending flat end face 42. The outer or movable carrier 34 is generally similar to the inner carrier 32 except that the outer carrier includes a pair of guide dowels 44 extending outwardly and receivable in the guide bores 38 in order to ensure that movement of the carriers 32, 34 will be accomplished without tilting or cocking of the carriers relative to each other. The movable carrier 34 includes a pocket 46 extending inwardly from the end face 48 opposite the end face 42 of the inner carrier 32. The pocket 46 is adapted to receive and position a load cell 50 which includes an end face 52 for a function to be described herein.

Figure 3:
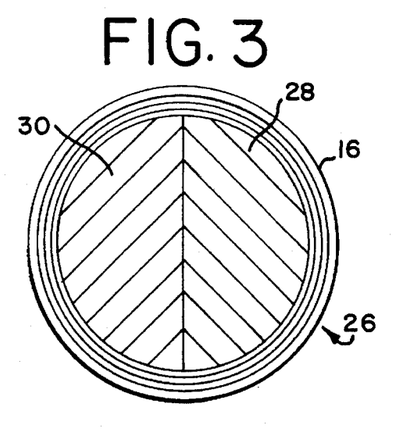
FIG. 3 is an enlarged, vertical sectional view of the split shaft portion of the apparatus of FIGS. 1 and 2, showing the same in the closed position.
Figure 4:
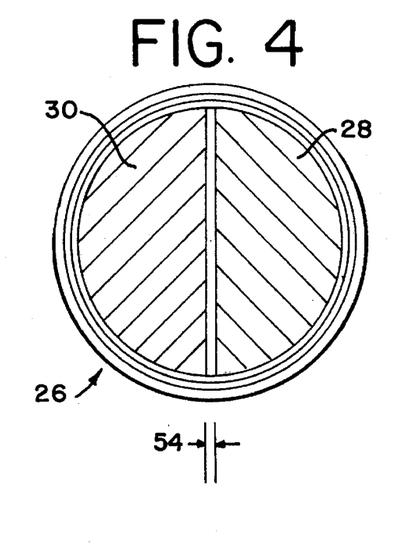
FIG. 4 is a view similar to that of FIG. 3, but showing the split shaft with two halves thereof in a spaced apart position.
Figure 5:
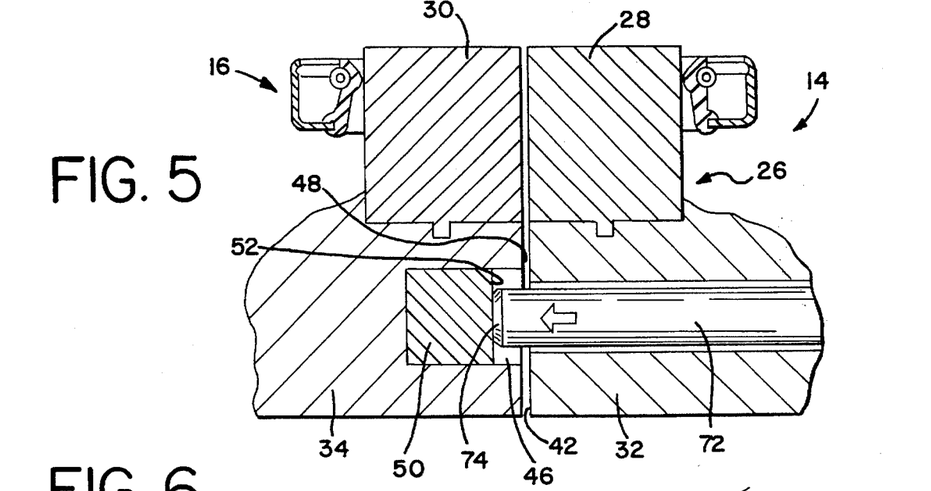
FIG. 5 is a still further enlarged vertical sectional view showing a seal of the type being tested in position over the shaft with the shaft having undergone a spreading movement.

As noted, the inner and outer shaft halves 28, 30 are respectively positioned atop their carriers 32, 34 and the carriers are movable such that the shaft halves may provide a split or opening 54 between them or may be closed down so that, as a pair, the shaft halves present a cylindrical body having a round cross-section. FIGS. 3–5 illustrate the movement of the halves 28, 30 between closed and open positions.

Referring now to the control portion of the test apparatus 10, FIGS. 1 and 2 show a micrometer assembly generally designated 56 secured by a mounting block 58 to an outer surface 60 of the oven wall 22. As is conventional, the micrometer includes a thimble 62 which surrounds a center body 64 having micrometer threads (not shown) thereon.

According to the known principles, rotation of the thimble moves the thimble axially relative to the center body, causing counterpart axial movement of the micrometer rod 66. The center body 64 is sometimes called the barrel or spindle of the micrometer screw and is conventional. A finger grip 68 with a preload and ratchet mechanism may be provided for accuracy of movement.

Further in accordance with the invention, the micrometer rod 66 terminates in an interior passage 70 within the oven sidewall 22. In opposed facing relation to the micrometer rod 66 is a rod extension 72 having a nose portion 74. In use, and referring again to FIG. 2, the nose portion 74 of the rod extension 72 contacts the end face 52 of the load cell. When the thimble 62 is rotated clockwise, the micrometer rod extends and moves the rod extension in such a way as to exert a force on the load cell and move the movable carrier 34 away from the fixed carrier. This splits the shaft and tends to move the oil seal or other annular body from a cylindrical shape to an oval shape. Because the annular specimen 16 is elastomeric, and because it has so-called "molded interference" it is a snug fit over the test shaft 26. Any movement of the shaft halves 28, 30 apart from each other will therefore tension the body of the seal.

Referring now to the operation of the apparatus, it will be assumed that a specimen product such as a completed oil seal 16 is to be tested in the apparatus and that the formulation of the elastomer and its physical properties in a given cure state are generally known as a result of prior testing operations. The seal itself includes a rigid metal casing 76 and an elastomeric body 78, and also includes a garter spring 80, which may or may not be used during the test process. The body 78 includes a lip portion 82 contacting the shaft 26.

The micrometer thimble 62 is manipulated so as to withdraw the micrometer rod 66 from the head or proximate end portion of the rod extension 72, leaving the extension shaft free to slide within the opening 40. Thereupon, the two halves 28, 30 of the split shaft 26 are manually pressed together into a tightly abutting relationship with the two end faces 42, 48 contacting each other. The specimen seal 16 is then placed over the shaft 26. Because the seal is made to a certain inside diameter (ID) which is slightly smaller than the outside diameter (OD) of the split shaft 26, there will be a certain amount of initial tension on the seal lip resulting from the differences in the size of the seal and the shaft. In other words, the seal is molded to a slightly smaller dimension than the shaft OD; this is "molded interference" that causes a radial compressive load to be applied to the shaft along the contact band of the seal when it is in use.

After being positioned as shown in FIG. 5, for example, the seal is allowed to attain the temperature of the oven interior (usually 212° F.) which temperature is noted. Next, the thimble is manipulated so as to advance the rod and move the rod extension toward engagement with the end face of the load cell. During this portion of its movement, the thimble will spin freely with no measurable resistance. When the nose portion 74 of the rod extension 72 contacts the end face 52 of the load cell 50, significant resistance will be met inasmuch as the two shaft halves are held together by the force exerted by the seal. The seal therefore causes the split shaft 26 to resist separation.

At this point, appropriate calibration adjustments are made so that the micrometer's initial position is considered zero and the force on the load cell is zero. Thereupon, the micrometer is manipulated rapidly until a displacement of 0.025 inches has been achieved. The movement of the thimble necessary to achieve this degree of shaft half separation will be resisted by the force applied to the end face 48 of the movable carrier 34, in turn caused by the tendency of the rubber seal body to move the shaft halves 28, 30 towards each other. The load cell, in a known manner, creates a voltage in response to the applied load which is read on an appropriate meter and noted. Customarily, the instrument is calibrated so that the output may be read in pounds.

As the 0.025 inch movement is completed, a timing process is begun and the load values are recorded, preferably on a strip chart recorder. Characteristically, the elapse of time will be represented by a generally horizontal trace which first decays rather rapidly and then tends to level off somewhat. At the end of a predetermined time, such as two minutes, the process is repeated. Thus, another 0.025 inch movement is rapidly accomplished and the load value noted on the chart. Again, the initial high value will decay somewhat and tend generally to level off before the two minute period elapses. This process is repeated through three to five cycles, with each movement increment being the same and each relaxation time being the same. The load values will be seen to vary in a characteristic pattern, depending on the cure state of the rubber.

Figure 6:
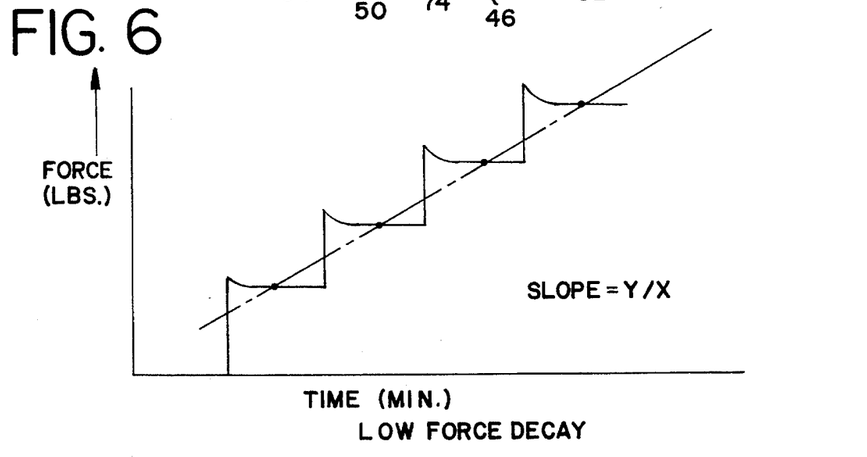
FIGS. 6 and 7 are graphs showing force/deflection characteristics, including force decay with time, in more and less completely cured specimens, respectively.

Referring now to FIG. 6, a typical such graph is shown. Here, the vertical axis or ordinate (Y axis) of the graph represents the force measured at the load cell and the abscissa or X axis of the graph represents the time in minutes. Such a graph, verbally expressed, shows that the equal successive deflections will be accompanied by a rise in the force or load, and that such force will decay, as time passes, to a certain extent.

Figure 7:
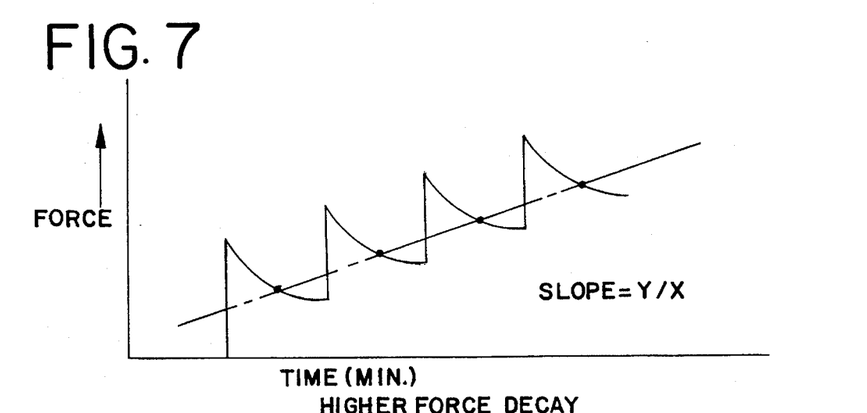

When a plot is made of such readings, it will typically appear in the form shown in FIG. 6. The decayed forces of each step are read, and a line is drawn to connect these force points against deflection points (FIG. 7). Such a line will then have a characteristic slope. The slope of the line will be steeper if the force decay with time is less than it would be if the decay were greater. FIG. 7 is an example illustrating another curve which is similar to FIG. 6 in that the height of each vertical step, representing the same degree of movement, is the same. However, because the force has decayed (the residual load is lower) after the same time, the slope of a line between steps will be lower than its counterpart wherein there was less decay.

According to the invention, for any given product, the slope of this line is determined and recorded for comparison purposes. As pointed out above, the slope of this line will be different for different products. However, a series of readings taken on a product intended to be identical, i.e., the same size, shape and material, the slope of the line just discussed may vary significantly.

According to the invention, it is this line that must be compared with a standard slope which represents the ideal cure for that particular product, made from a particular material. Accordingly, the use of the method pre-supposes that a number of specimens of a given product made from a given material have been manufactured and analyzed as to physical properties. Among such specimens, some will be intentionally under-cured, others will be intentionally over-cured, and still others will have at least to a certain extent, an ideal cure state. Typically, the under-cured products will display less "followability" or fewer of the characteristics of the true elastomer, and the over-cured products will be unduly stiff, tending towards being rigid and/or brittle. Assuming, by way of example, that five of such specimens have been prepared, merely by way of example, each is tested to determine a series of force/deflection readings as just described and the slope of the line is determined and noted. Thereafter, each seal is analyzed by the Flory-Rehner method of soaking and solvent and allowing the article to swell until it reaches equilibrium, usually requiring more than 72 hours in addition to several hours of drying time. The cross-link density is then expressed as a number falling within the range of 0.1 to about 0.4, and normally in a narrower range of about 0.2 or less up to 0.3 or slightly higher. The particular number will depend on the rubber material being used.

Figure 8:
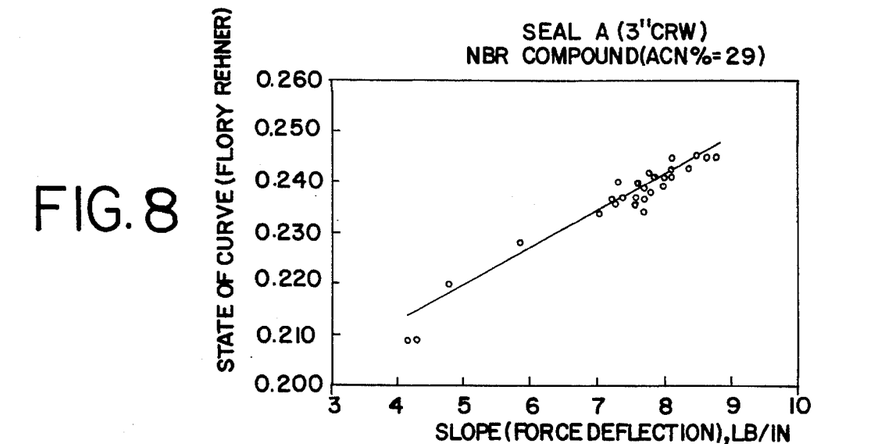
FIGS. 8–10 are graphs showing the relation of the state of cure determined by an accepted method in relation to the slopes of various force/deflection curves derived from testing particular rubber products made from differing formulations.

Assuming, for the moment, and referring now to FIG. 8, that the specimens tested revealed a force/deflection curve, expressed in pounds per inch, of having values in the case of an under-cured product of about 5, and an over-cured product, just less than 9, and that satisfactory products demonstrated a force/deflection slope from about 7.2 to about 8.5, it would be noted that the state of cure for the satisfactory products would have a cross-link density from about 0.23 to about 0.245. Consequently, according to the invention, with such cross-link density having been found to be ideal, and with such cross-link density corresponding to a force/deflection curve slope of between 7.2 and 8.5, then, as long as the products in question displayed a force/deflection curve with a slope of about 8, when tested as described above, then such products would be ideally cured. If, for such a product, the slope of such curve began to exceed about 8.2 or 8.3, a tendency towards over-curing would be present and would be compensated for in process conditions. Likewise, a drop of the slope below about 7.3 would indicate that additional cure time and/or temperature should be used.

Referring now to others details of the test method, prior art established standard methods of testing elastomers for a cure state depend on eliminating or minimizing Van der Waal's forces in the rubber composition. These forces are a source of attraction between internal elements of the rubber, but are found to be reduced to a low value with the passage of time. Hence, after a measurable time interval at elevated temperatures, the effect of Van der Waal's forces reduces materially or disappears and cross-link density becomes the only significant force then being measured. Typically, after a two minute period of relaxation at a temperature of 100° C. (212° F.) a specimen will have undergone 95–99% of the relaxation that it will exhibit within 24 hours. Consequently, a two minute interval is sufficient to perform the method of the invention.

Obviously, the slope of the line in question will vary with the units selected for distance and the graphic interval selected for the time measurements. However, the difference in slope will be visible and intervals should be selected wherein the slope differences are readily able to be visualized.

Figure 9:
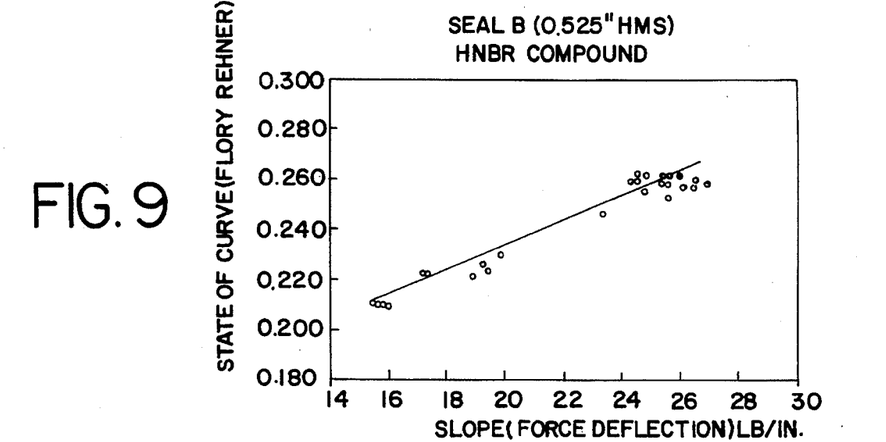
Figure 10:
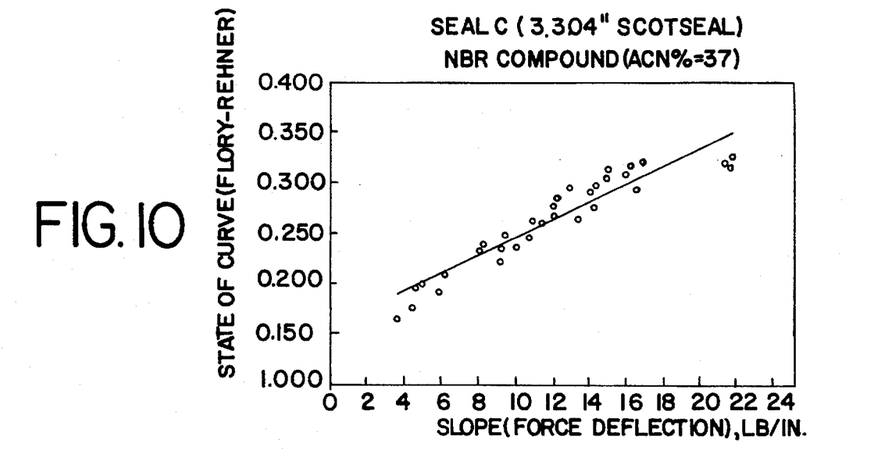

Referring now to FIGS. 8–10, a graphic representation of the inventive method is shown. Here, the vertical axis or ordinate of the graph consists of numbers indicative of the cross-link density as measured by the Flory-Rehner method. In FIG. 8, the state of cure varies between 0.200 and 0.260. On the horizontal axis, the slope of the force/deflection curve is expressed as varying from 3 to 10. The various data points on the graph show slopes varying between 4 and 9. The line drawn to connect these points, as determined by the center line average method, merely shows that slopes and cure states vary proportionately, within fairly narrow limits. Based on other tests, it has been hypothetically determined that a cure state of 0.230 to 0.245 is desirable for a cured rubber product of a certain size and shape, made with a typical rubber such as a nitrile or buna N rubber. Where the slope of the force/deflection curve for this particular seal, expressed in pounds per inch lies between 7 and 9, then a cure state of 0.23 to 0.245 is indicated and this is considered ideal for the particular application.

Referring to FIG. 9, a similar graph is shown. Here, the desired cure state centers around a Flory-Rehner value of about 0.26. This corresponds to a force/deflection curve slope of about 24–28, where the force/deflection is expressed in pounds per inch and the size of the seal product is very small. Hence, the seal is stiff and the slope is steep. Thus, a seal having an inside diameter of 0.525 inches and made from what is termed an HNBR rubber compound will have a force/deflection slope which is considerably greater than that of a 3 inch diameter seal, such as that shown in FIG. 8. In this connection, it will be apparent that the force/deflection characteristics depend on the material and itself as well as the effective cross-section of the specimen and the diameter. Thus, at the extremes, a small diameter seal with a thick cross-section is much stiffer, i.e., has a higher spring rate than a large diameter seal with a very thin cross-section. In most seals, the diameter and the cross-section vary generally in a direct relation, but their force/deflection curves are different for different applications.

Referring to FIG. 10, another set of data are shown wherein the data points represent slopes varying from less than 4 up to almost 22. If a cure state of about 0.27 to about 0.32 is desired, as established by prior tests, then the force/deflection curve should have a slope of from about 14 to about 18. In this connection, it will be noted that the straight lines shown in FIGS. 8–10 are not the lines whose slope is being considered. These are merely lines indicating that there is a proportion between the Flory-Rehner cure state and the slope of any one set of force/deflection curves.

Thus, in keeping with the invention, where it is desired to develop an ideal product, a specimen with ideal end use characteristics is produced and such a specimen is tested for physical properties. Thereafter, the specimen is treated by the Flory-Rehner method, which involve a long soaking in solvent and which is a destructive test. The Flory-Rehner value indicative of its cure state is noted and a similarly cured seal is analyzed in terms of the slope of its force/deflection curve. Thereafter, the force/deflection curves of randomly selected specimens are periodically measured according to the invention and their slopes are used in such a way as to control curing. Thus, if a typical seal had a force/deflection curve slope of 5 in an ideal product, then as the slope of the force/deflection curve of samples taken periodically during manufacture began to increase beyond 5, shorter cure times or lower temperatures would gradually be phased into the manufacturing process. Similarly, as the slope began to decrease below 5, cure times and temperatures would be increased until specimens showed the slope values within the desired range.

By way of explanation, and referring now generally to the matter of testing for degree of cure in a finished specimen or product, the general behavior of elastomeric materials during curing should be considered. In this connection, an elastomeric formulation having one or more basic polymers, cross-linking agents, processing aids, fillers, and like materials known to those skilled in the art are normally quite viscous and plastomeric at room temperature, and present a tacky surface.

As heat is applied during the molding process, the material initially remains uncured and loses viscosity, appearing to melt with an increase of temperature. However, the temperature increase serves to activate the catalyst/curing system and a cross-linking reaction begins to take place wherein a three dimensional molecular network is formed. As time passes, the rubber material undergoes a continuing temperature increase, not only from its contact with the mold, but also by reason of the exotherm developed from the cross-linking reaction. Particularly inasmuch as the most rubbers are excellent heat insulators, a rapid rise in temperature and a corresponding rise in viscosity occurs. Within a short time, the material becomes substantially cross-linked and completely resistant to flow. At this point, its viscosity, properly so called, is no longer in question, inasmuch as it will not undergo viscous shear when subject to a force. Instead the rubber acts as a solid, elastomeric material with a characteristic stress/strain or force/deflection curve. The change of this property with temperature, i.e., stress relaxation behavior at different temperatures, is the principle used in the practice of the invention.

With rubber materials which are not completely cured, their behavior is different at least in degree, from those that are fully cured. Thus, when a given specimen of rubber is first elongated, the requisite force to create or maintain the elongation has a certain value. After an initial force causes a given deflection with time, due to stress relaxation behavior, the force will gradually decay until it reaches a relatively fixed level. The extent of relaxation with time, particularly at an elevated temperature, is a characteristic which, according to the present invention, is indicative of the cure state of the material. Thus, a less well cured material is slightly less elastic than a more fully cured material. When a plot of force vs. time at a series of deflections is made, the greater the force/deflection slope, the higher the cure state. When a graph showing a series of such readings is prepared, a relatively less cured material will have a force/deflection curve with a rather shallow slope, i.e., the value of Y relative to X will be lower than in a more fully cured product.

In the prior art, lengthy, destructive tests were required to determine the state of cure or degree of cross-linking in the material.

The described method and apparatus thus provide a quick, economical and reproducible method of obtaining correspondence between processing conditions and finished behavior in a non-destructive manner.

It will thus be seen that the present invention provides an analyzer and method for rapid, non-destructive determination of the state of cure of finish molded rubber articles having a number of advantages and characteristics including those expressly pointed out here, and others which are inherent in the invention. An illustrative embodiment of the product of the invention having been shown and described, it is anticipated that variations to the described form of apparatus will occur to those skilled in the art and that such modifications and changes may be made without departing from the spirit of the invention, or the scope of the appended claims.

We claim:

1. A method of rapidly determining the cure state of a molded rubber article, said method comprising controlling the temperature of an annular elastomeric article whose cure state is to be measured to such that said temperature is at least 90° C., placing said article over a test fixture having separable parts, said article being sized so that radially inner portions of said article engage said test fixture with an interference fit, repeatedly moving said separable parts away from each other in steps of equal, predetermined distances so as to tension said article stepwise, each of said steps being a small proportion of the total elastic deformation able to be undergone by said article, permitting the tension induced by said movement of said separable parts to relax for a given time period following each tensioning step, measuring the tensile force remaining in said test article after each of said tensioning and relaxation steps, using the values of the forces and deflections thus generated to determine a force/deflection line having a given slope characteristic of that article during plural successive tensioning and relaxation steps, and thereafter comparing the slope of said force/deflection line with the slope of a force/deflection line characterizing successive tensioning and relaxation steps of an optimally cured rubber article made in the same size, shape and from the same material as determined by a prior empirical method, thereby determining the extent to which the cure state of said tested article corresponds to that of an article having an optimal cure state.

2. A method as defined in claim 1 wherein said temperature is at least 100° C.

3. A method as defined in claim 1 wherein said elastomeric article is an oil seal having an inside diameter of from about 0.5 inches to about 6 inches and wherein said predetermined distances are from about 0.01 to about 0.05 inches.

4. A method as defined in claim 1 wherein said given time permitted for relaxation of induced tension is less than two minutes for each tensioning step.

5. A method as defined in claim 1 wherein said elastomeric article is an oil seal having a metal casing portion and an annular rubber body including a seal lip portion.

6. A method as defined in claim 1 wherein said prior empirical method is the Flory-Rehner method.

7. A method of controlling the cure state of a plurality of articles each having an annular rubber body portion and being manufactured in serial production, said method comprising the steps of continually producing a plurality of said articles by molding said rubber body for a first time at a first temperature, periodically removing specimen test articles being produced by said production process, placing each of said test articles in an elevated temperature atmosphere so as to permit relaxation of said rubber body portion of said articles, elongating each specimen to a predetermined extent and measuring the forces resisting such elongation after elapse of a predetermined relaxation time, and repeating such elongation, relaxation and force measuring steps so as to determine a set of force/deflection values, expressing such values as a force/deflection line having a given slope, comparing the slope of the line thus produced with the slope of a force/deflection line displayed by a previously manufactured article displaying optimal cure characteristics, and increasing at least one of said cure time and temperature where the specimen article displays a lower slope than said optimal slope, and decreasing at least one of said cure time and temperature when said specimen article displays a force/deflection slope which is steeper than said optimal force/deflection slope.

8. A method as defined in claim 7 wherein said articles are oil seals each having a casing portion and an elastomeric body portion.

9. A method as defined in claim 7 wherein the time taken for each of said relaxation steps is two minutes or less.

10. An apparatus for determining the slope of a force/deflection curve generated by elastomeric articles having an annular cross section, said apparatus comprising a cylindrical test shaft adapted to receive an annular test specimen thereover in surrounding relation such that portions of said test specimen engage the surface of said shaft with an annular contact pattern, said shaft being split into first and second shaft halves along a given plane centrally of said shaft, a fixed shaft half carrier secured to said first shaft half and a movable shaft half carrier secured to said second shaft half, said carriers being constructed and arranged so as to move bidirectionally along a plane perpendicular to said shaft central plane, a pocket in said movable carrier and a load cell having an exposed end face disposed within said pocket, a rod-receiving passage extending through said fixed carrier, means for securing a part of said first carrier to an oven wall, and a force-applying assembly to cause said movable carrier to move, said force-applying assembly including a finely threaded body portion and a rotatable thimble carried by and threadedly engaging said body portion, said thimble including a contact end face, and an operating rod extending outwardly from said contact end face of said thimble through said passage in said fixed carrier and toward said end face of said load cell, said apparatus being constructed and arranged so that rotating said thimble causes said operating rod to engage said end face of said load cell and displace said movable carrier away from said fixed carrier by an amount indicated by the rotational position of said thimble, said load cell being operatively connected to a unit for indicating the resistive force generated by relative movement of said first and second shaft halves when a specimen is positioned over said test shaft in snug relation.

* * * * *